(12) United States Patent
Sweeney

(10) Patent No.: US 9,994,381 B2
(45) Date of Patent: Jun. 12, 2018

(54) NO DRIP TRAY LINER

(71) Applicant: Shaun Sweeney, Wayne, NJ (US)

(72) Inventor: Shaun Sweeney, Wayne, NJ (US)

(73) Assignee: Cygnus Medical, LLC, Branford, CT (US)

( * ) Notice: Subject to any disclaimer, the term of this patent is extended or adjusted under 35 U.S.C. 154(b) by 414 days.

(21) Appl. No.: 14/729,819

(22) Filed: Jun. 3, 2015

(65) Prior Publication Data
US 2015/0266649 A1 Sep. 24, 2015

Related U.S. Application Data

(63) Continuation of application No. 12/727,684, filed on Mar. 19, 2010, now Pat. No. 9,062,914.
(Continued)

(51) Int. Cl.
*B65D 81/26* (2006.01)
*B32B 29/00* (2006.01)
(Continued)

(52) U.S. Cl.
CPC .............. *B65D 81/264* (2013.01); *A61L 2/26* (2013.01); *B32B 3/266* (2013.01); *B32B 5/18* (2013.01); *B32B 7/04* (2013.01); *B32B 27/10* (2013.01); *B32B 27/40* (2013.01); *B32B 29/00* (2013.01); *B32B 29/007* (2013.01); *B32B 29/06* (2013.01); *B65B 55/02* (2013.01); *B65B 55/20* (2013.01); *B65D 81/057* (2013.01); *F26B 5/16* (2013.01); *A61L 2202/182* (2013.01); *A61L 2202/24* (2013.01); *B32B 27/36* (2013.01); *B32B 2250/02* (2013.01); *B32B 2266/0264* (2013.01); *B32B 2266/0278* (2013.01);
(Continued)

(58) Field of Classification Search
None
See application file for complete search history.

(56) References Cited

U.S. PATENT DOCUMENTS 3,205,120 A 9/1965 Flanders
3,228,820 A 1/1966 Samson
(Continued)

OTHER PUBLICATIONS

Jangro, Wiping, Nov. 2008.*

*Primary Examiner* — Jeffrey A Vonch
(74) *Attorney, Agent, or Firm* — St. Onge Steward Johnston & Reens, LLC

(57) ABSTRACT

The present invention is directed to a two-ply absorbent liner for use in a sterilization process and, more particularly, to an absorbent liner having a foam layer and a paper layer for cushioning sterilization trays and surgical instruments in a sterilization pack and providing advantageous moisture absorption functionality during and after completion of a sterilization process. The absorbent liner functions advantageously with steam or ethylene oxide gas as the sterilization agent. The absorbent liner is fabricated from a foam material, preferably a hydrophilic polymeric foam material, e.g., a hydrophilic polyurethane foam flame laminated to paper, preferably medical grade paper. The disclosed liner may be advantageously utilized in sterilizing surgical instruments and in conjunction with sterilizing trays such that potential residual moisture is eliminated from the surface of the instruments or trays and metal surfaces are cushioned.

20 Claims, 4 Drawing Sheets

Related U.S. Application Data

(60) Provisional application No. 61/161,688, filed on Mar. 19, 2009.

(51) Int. Cl.
  *B65B 55/02* (2006.01)
  *B65B 55/20* (2006.01)
  *B65D 81/05* (2006.01)
  *B32B 29/06* (2006.01)
  *B32B 7/04* (2006.01)
  *B32B 5/18* (2006.01)
  *B32B 27/10* (2006.01)
  *B32B 27/40* (2006.01)
  *F26B 5/16* (2006.01)
  *A61L 2/26* (2006.01)
  *B32B 3/26* (2006.01)
  *B32B 27/36* (2006.01)

(52) U.S. Cl.
  CPC ..... *B32B 2305/022* (2013.01); *B32B 2307/54* (2013.01); *B32B 2307/5825* (2013.01); *B32B 2307/72* (2013.01); *B32B 2307/724* (2013.01); *B32B 2307/726* (2013.01); *B32B 2307/728* (2013.01); *B32B 2439/02* (2013.01); *B32B 2439/80* (2013.01); *B32B 2535/00* (2013.01); *Y10S 428/906* (2013.01); *Y10T 428/15* (2015.01); *Y10T 428/24322* (2015.01); *Y10T 428/249953* (2015.04); *Y10T 428/249987* (2015.04)

(56) References Cited

U.S. PATENT DOCUMENTS

| | | | |
|---|---|---|---|
| 3,285,800 A | 11/1966 | Bartell et al. | |
| 3,314,425 A * | 4/1967 | Coppick | A61F 13/00042 264/266 |
| 3,366,532 A | 1/1968 | Maskey et al. | |
| 3,396,419 A * | 8/1968 | Richter | A47K 7/03 15/104.93 |
| 3,431,911 A | 3/1969 | Meisel, Jr. | |
| 3,503,838 A | 3/1970 | Marshack | |
| 3,530,030 A | 9/1970 | Adams et al. | |
| 3,533,901 A * | 10/1970 | Sutker | D21H 19/824 156/79 |
| 3,563,243 A * | 2/1971 | Lindquist | A61F 13/15 604/369 |
| 3,668,050 A * | 6/1972 | Donnelly | A61B 46/00 128/849 |
| 3,677,858 A | 7/1972 | Sokolowski | |
| 3,687,797 A | 8/1972 | Wideman | |
| 3,738,359 A * | 6/1973 | Lindquist | A61B 46/23 128/852 |
| 4,142,632 A * | 3/1979 | Sandel | A61B 50/30 206/363 |
| 4,276,339 A | 6/1981 | Stoveken | |
| 4,720,410 A | 1/1988 | Lundquist et al. | |
| 4,798,292 A | 1/1989 | Hauze | |
| 4,822,669 A | 4/1989 | Roga | |
| 5,082,707 A * | 1/1992 | Fazio | A47G 9/062 428/43 |
| 5,164,421 A | 11/1992 | Kiamil et al. | |
| 5,174,306 A * | 12/1992 | Marshall | A61F 15/001 128/849 |
| 5,435,971 A | 7/1995 | Dyckman | |
| 5,447,962 A * | 9/1995 | Ajioka | C08J 9/06 521/182 |
| 5,804,512 A * | 9/1998 | Lickfield | D04H 3/14 156/269 |
| 5,947,122 A * | 9/1999 | McDonald | A61B 46/00 128/849 |
| 6,245,697 B1 * | 6/2001 | Conrad | C08F 220/18 428/304.4 |
| 6,248,293 B1 | 6/2001 | Davis et al. | |
| 6,391,260 B1 | 5/2002 | Davis et al. | |
| 6,406,764 B2 * | 6/2002 | Bayer | A61L 2/07 206/438 |
| 6,440,375 B1 | 8/2002 | Davis et al. | |
| 6,548,727 B1 * | 4/2003 | Swenson | A61L 15/26 602/41 |
| 6,902,712 B2 | 6/2005 | Davis | |
| 7,565,972 B2 | 7/2009 | Steppe | |
| 7,862,686 B2 | 1/2011 | Ward et al. | |
| 2002/0064478 A1 | 5/2002 | Davis | |
| 2002/0197424 A1* | 12/2002 | Bayer | A61L 2/26 428/34.2 |
| 2004/0071490 A1* | 4/2004 | Vosbikian | A47L 13/12 401/49 |
| 2005/0079093 A1* | 4/2005 | Cannady | A61L 2/28 422/1 |
| 2005/0136238 A1 | 6/2005 | Lindsay et al. | |
| 2006/0008633 A1* | 1/2006 | Chan | B32B 5/24 428/304.4 |
| 2006/0067855 A1* | 3/2006 | Mathis | A61B 50/30 422/28 |
| 2006/0068674 A1* | 3/2006 | Dixit | A61L 2/26 442/412 |
| 2006/0246272 A1* | 11/2006 | Zhang | A61F 13/53708 428/304.4 |
| 2007/0023309 A1 | 2/2007 | Davis | |
| 2007/0026472 A1* | 2/2007 | Prokash | A61L 2/07 435/7.32 |
| 2007/0095699 A1 | 5/2007 | Frieze et al. | |
| 2007/0148432 A1* | 6/2007 | Baker | A61L 15/425 428/304.4 |
| 2007/0191502 A1* | 8/2007 | Free | C08G 18/4202 521/172 |
| 2007/0225669 A1* | 9/2007 | Dyer | A61F 13/2065 604/369 |
| 2007/0253864 A1 | 11/2007 | Maguire, Jr. et al. | |
| 2008/0210225 A1* | 9/2008 | Geiger | A61M 15/0086 128/200.14 |
| 2008/0213566 A1* | 9/2008 | Chan | B32B 5/24 428/319.3 |
| 2009/0075026 A1 | 3/2009 | Vito et al. | |
| 2009/0118387 A1* | 5/2009 | Sakakibara | A61L 15/26 521/170 |
| 2010/0190004 A1* | 7/2010 | Gibbins | A61F 13/02 428/346 |
| 2010/0215942 A1 | 8/2010 | Casati et al. | |
| 2011/0052863 A1* | 3/2011 | Sweeney | B32B 5/18 428/137 |

* cited by examiner

NO DRIP TRAY LINER

FIELD OF THE INVENTION

The present invention relates to liners such as tray liners for use in a sterilization process, and more particularly to an absorbent two-ply liner providing an advantageous moisture absorption functionality during and after completion of a sterilization process. The liner may be used as a base pad, a tray corner guard, or for cushioning of surgical instruments during and after the sterilization process.

BACKGROUND OF THE INVENTION

As is well known, surgical instruments used in the healthcare industry must be sterilized before and/or after each use. Sterilization, of course, frees instruments from microorganism contamination, to prevent infections and the spread of diseases among patients. All medical procedures rely upon a stringent program of sterilization.

The medical device industry has addressed the sterilization requirements in the surgical field by offering two general types of surgical instruments: reusable instruments and single use, or disposable, instruments. Reusable instruments are typically composed of stainless steel and are typically sterilized before their initial use and then cleaned and resterilized prior to each subsequent use thereof. Single use or disposable instruments, on the other hand, are often fabricated primarily from plastic materials, thereby reducing costs associated with manufacture, and are discarded after use in a single procedure.

With respect to reusable surgical instruments, e.g., forceps, graspers, dissectors, probes, hemostats, scissors and the like, sterilization and resterilization had historically been accomplished using various sterilization modalities. In a broad sense, these sterilization processes generally involve placing instruments to be sterilized in a tray, wrapping the instruments and the tray with a sterilization wrap, and placing the wrapped tray and instruments in a sterilization chamber, where the instruments are exposed to a sterilization medium. In order to protect the instruments, a tray liner is typically placed on the tray, and then the surgical instruments are placed on the tray liner. In order to protect the tray itself, the tray is typically placed on corner guards or a base pad before it is wrapped and placed in the sterilization chamber.

One long and continuing problem encountered with sterilization, however, is the presence of moisture that remains on the sterilized instruments, i.e., within the sterile wrap, at the conclusion of the sterilization process. This residual moisture can range from slight levels of dampness to visible droplets on the surface of surgical instruments. Such residual moisture is both undesirable and is unacceptable because such moisture could permit migration of surface microorganisms, thereby penetrating the wrapped tray or basin and rendering its contents contaminated, and/or may cause rust or pitting of the surgical instruments. Also, the wrapped tray may become stained during sterilization or even torn during loading or removal from a sterilization chamber because of the damp condition of the sterilization wrap.

Tray liners formed of a single material, such as open or closed cell foam or a cellulose based material have been employed in the past. For example, a hydrophilic polyurethane foam trayliner is disclosed in U.S. Pat. No. 6,902,712, incorporated herein by reference. This tray liner is comprised of a single foam layer. While effective, the evaporation rate and dispersing properties of foam liners could be improved to allow for more efficient moisture absorption and multiple applications within in a sterilization system.

Two-ply liners comprised of foam backing are known in the art. Typically a foam layer is adhered to plastic or cloth. However, use of adhesive to join liners used for sterilization presents several problems. The adhesive may deteriorate when exposed to high heat, steam and/or various chemicals used in the sterilization process. The liners may delaminate or adhesive may come in contact with the sterile instruments or sterilizing equipment. The adhesive residue is often sticky and difficult to eliminate.

In addition, laminated paper products which contain at least one layer of paper bonded to a foam layer have also been known for some time. See e.g. U.S. Pat. Nos. 3,687,797; 3,285,800; 3,530,030; 3,366,532. However, these multi-layered products are also adhered together with an adhesive or thermally fused with hot rollers. U.S. Pat. No. 4,276,339 discloses a more efficient lamination process via a gelling process; however it does not allow the paper and foam to be separately purchased.

A two-ply liner comprised of foam and paper joined by flame lamination has never been taught for the purpose moisture trapping, and more specifically for use in sterilization of surgical instruments.

SUMMARY OF THE INVENTION

The present invention is intended to obviate many of the problems associated with moisture remaining on or in the trays after a sterilization process. Rather than employing a tray liner formed of a single material, such as open or closed cell foam or a cellulose based material, as has been done in the past, the present invention employs a two-ply construction to provide padding as well as absorption. More specifically, the present invention combines the cushioning properties of foam with the absorbent properties of medical grade paper in order to protect delicate instruments from impact damage as well as preventing the adverse effects of moisture, and also to trap moisture and provide protection when used as a base pad or corner guard.

As exemplified in the Figures and described in detail herein, when used as a tray liner, it has been found that positioning the inventive material with the foam layer adjacent to instruments, such that the instruments are in contact with the foam layer, provides excellent results. The instruments are well-protected and the moisture is retained in the paper layer, away from the instruments, where it spreads out through the paper in order to increase the surface area of the moisture and also thereby increase the rate of evaporation.

When used as a base pad or corner guard, it has been found that positioning the inventive material with the paper layer adjacent to the tray, such that the tray is in contact with the paper layer, provides excellent results. The tray is well-protected, and the moisture is trapped in the paper layer before it reaches the sterile wrap. Also again, the moisture spreads out through the paper in order to increase the surface area of the moisture and also thereby increase the rate of evaporation.

The inventive material may employ any of numerous types of foam material, although polyester polyurethane foam has exhibited excellent results. The inventive material may also employ any of numerous types of medical grade paper, as well.

The foam layer and the paper layer are joined together using a flame lamination technique. As is known, such a technique involves passing the foam layer through an open flame, thereby creating a thin layer of hot polymer. The hot polymer is then used as an adhesive to bond the foam layer to the paper layer to create the inventive material. By employing this method, excellent results are achieved without the need for a separate adhesive, the use of which may have its own disadvantages.

BRIEF DESCRIPTION OF THE DRAWINGS

So that those having ordinary skill in the art to which the disclosed liner and associated methods pertain will more readily understand how to employ and use the same, reference may be had to the drawings wherein.

DETAILED DESCRIPTION OF THE INVENTION

Figure 1:
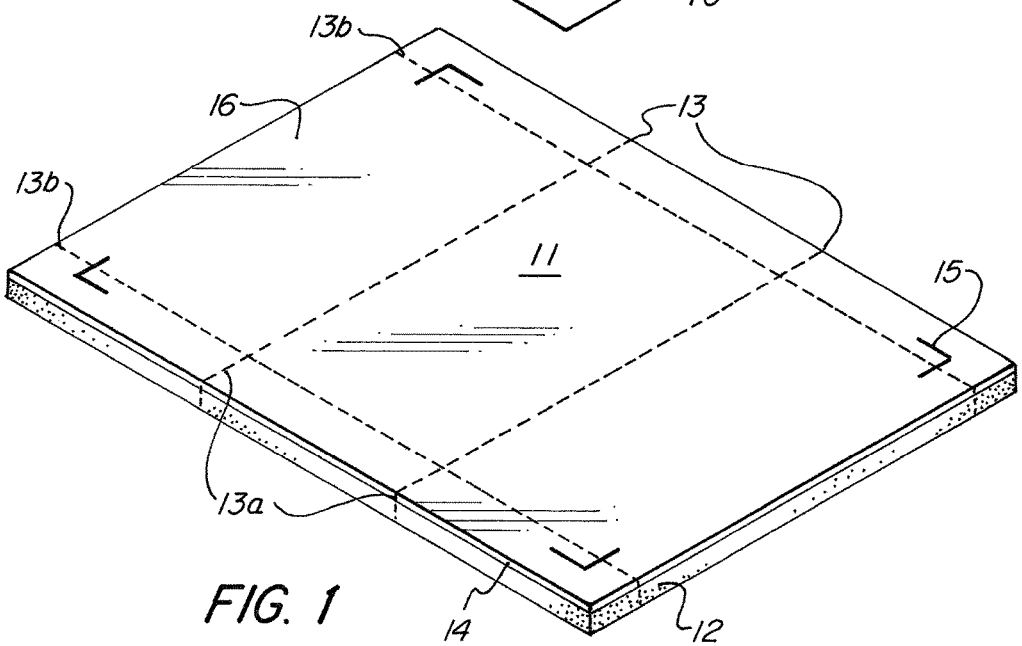
FIG. 1. is a perspective view of a two-ply liner according to the present invention.
Figure 5:
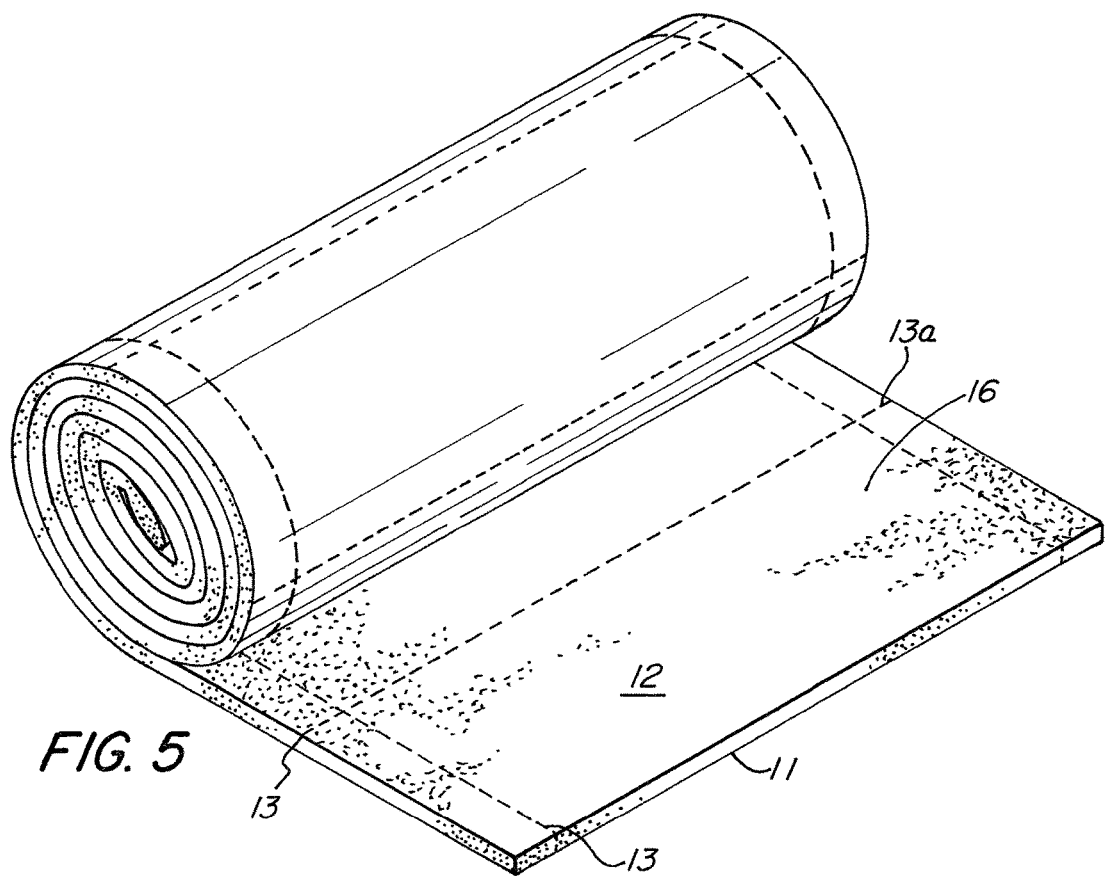
FIG. 5 is an alternate perspective view of tray liners according to the present invention.

Referring to FIGS. 1 and 5, a two-ply liner of the present invention is illustrated. In particular, an absorbent liner 16 is provided for introduction into a sterilizing system in connection with the sterilizing process. Liner 16 is composed of two layers 11 and 12. A paper layer 11 is composed of any type of paper that will allow moisture to be absorbed and dissipate. However, medical grade paper is preferred for use in sterilization systems. A foam layer 12 is preferably fabricated from hydrophilic polyurethane foam that is adapted for use in sterilization processes that utilize steam or ethylene oxide as the sterilizing agent.

The foam layer 12 is joined to the paper layer 11 at interface 14 through flame lamination. Flame lamination overcomes problems of the adhesives of the prior art. First, flame lamination does not have a tendency to delaminate when exposed to high temperatures, such as those used in the sterilization process. Flame lamination also prevents adhesive from leaking onto or contacting a tray or sterile instruments and consequently leaving an undesirable residue.

As shown, absorbent liner 16 is of rectangular configuration; however, alternative geometries are contemplated, e.g., as may be appropriate for specific sterilization tray configurations. Absorbent tray liners 16 may be dimensioned depending upon the application. Preferred absorbent liners 16 measure 9 to 15 inches in width and 0.1 inches to 1 inch in thickness. More preferred absorbent liners 16 measure 9, 12 or 15 inches in width, and are approximately ⅛ inch in thickness. Tray liner 16 preferred for use in separating basins measures 3×24 inches and may also be ⅛ inch in thickness.

The liner 16 may also be supplied in roll form as depicted in FIG. 5. When provided as a continuous roll, a length of 35 to 40 feet is preferred.

The liner 16 may, optionally, contain perforations 13. Latitudinal perforations 13a and longitudinal perforations 13b may be provided. The latitudinal perforations 13a allow the liner 16 to sit flatly on a surface since it has a tendency to curl. Moreover, the latitudinal perforations 13a allow the liner to be torn off a continuous roll, as depicted in FIG. 5. The latitudinal perforations 13a may be placed at any suitable interval so that the length of the liner can be chosen to accommodate sterilization trays of different sizes. Preferably the perforations 13 are about 2 to 3 inches apart. Most preferably, the latitudinal perforations 13a are spaced about 2 inches apart.

The liner 16 may also, optionally, contain surface cuts 15 in the paper layer 11 for purposes of corner relief, as discussed in more detail below. The cuts 15 are placed into the paper layer by any suitable means.

The absorbent liner 16 of the present invention is particularly adapted for use in a steam sterilization system or ethylene oxide sterilization system. As is known, sterilization systems generally include a sterilization chamber that is adapted to receive instruments to be sterilized, and a source of sterilizing agent, e.g. steam or ethylene oxide, connected to the sterilization chamber.

Preferably, the absorbent liner 16 is fabricated from a non-woven, lint free material that is compatible with both steam and ethylene oxide sterilization. The absorbent liner 16 is preferably fabricated from a hydrophilic polymeric foam plastic, e.g. a hydrophilic polyurethane foam that is clickable.

Typical physical properties of the foam include the following:

| Physical Properties | Minimum | Average |
| --- | --- | --- |
| Density (lbs./ft$^3$) | 1.60 ± 10% | |
| Tensile strength (psi) | 17.0 | 25.0 |
| Elongation (%) | 80 | 120 |
| Tear resistance (pli) | 1.20 | 1.90 |
| Compression force Deflection (psi) | | |
| 25% Deflection | 0.60 | 0.85 |
| 50% Deflection | 0.70 | 0.95 |
| Retention of Tensile Strength after 3 hours, 105° C., steam autoclave (%) | Minimum 70 | |
| Retention of Tensile Strength after 22 hours, 140° C., dry heat aging (%) | Minimum 70 | |

Figure 2:
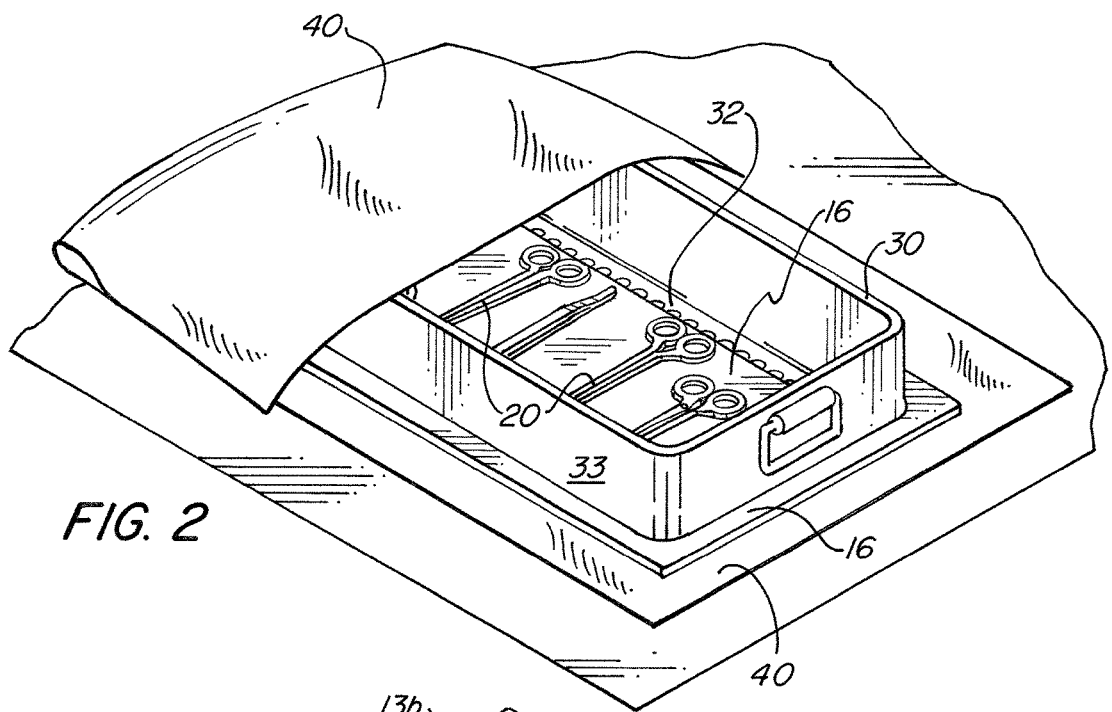
FIG. 2 depicts a perspective view of a sterilization system having various placements of an absorbent two-ply liner of the invention.
Figure 3:
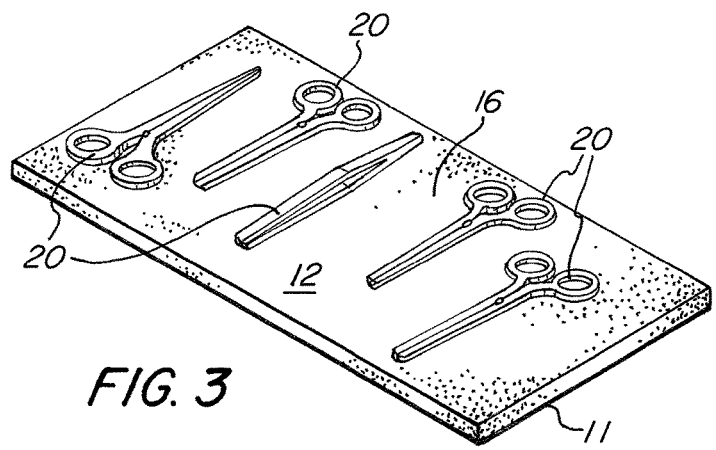
FIG. 3 is a perspective view of a tray liner according to the present invention, lying beneath surgical instruments.
Figure 4:
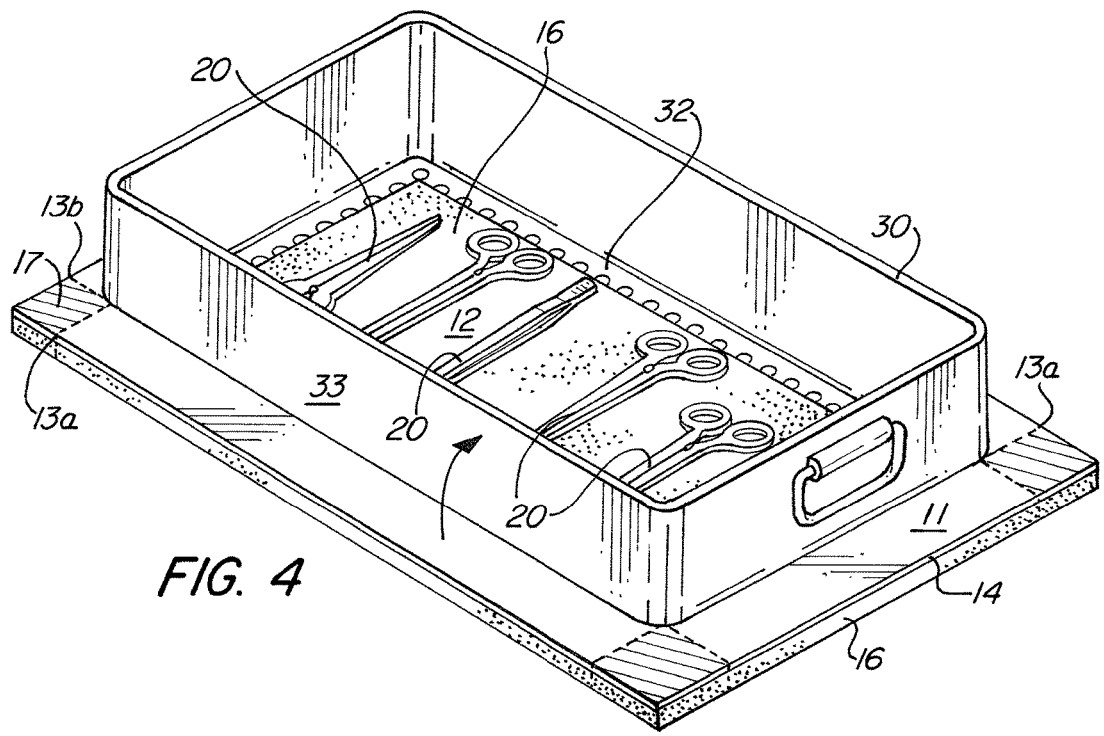
FIG. 4 is a perspective view of a two-ply liner according to the present invention, lying beneath surgical instruments and lying below a sterilization tray.

With reference to FIGS. 2, 3 and 4, a first embodiment of an absorbent liner 16 of the present invention is illustrated as a tray liner. The absorbent tray liner 16 of the present embodiment advantageously functions to prevent the presence of residual moisture on the surface of surgical instruments 20 at the conclusion of the sterilization process by absorbing such potential residual moisture. The surgical instruments 20 are positioned adjacent to the foam layer 12. Since the paper layer 11 is not adjacent to the surgical instruments, but rather below the foam layer 12, it pulls moisture from the foam layer 12 and retains any residual moisture. The moisture is free to spread out through the paper to increase the surface area of the moisture and thereby increase the rate of evaporation. Thus, the foam layer 12 advantageously cushions surgical instruments to be sterilized, e.g., forceps, graspers, dissectors, probes, hemostats, scissors and the like, both during and after the sterilization process and will not leave residual moisture on surgical instruments 20.

With reference to FIGS. 2 and 3, absorbent tray liner 16 generally comprises a sheet of absorbent material cut to substantially cover a base 32 of a sterilization tray 30. The base 32 of the sterilization tray 30 may be solid or perforated, as is known in the art.

FIG. 4 shows a second embodiment of an absorbent liner 16 of the present invention as a base pad. The absorbent liner 16 of the base pad embodiment advantageously functions to pull and retain moisture away from wrap 40 during and at the conclusion of the sterilization process by absorbing such potential and residual moisture. The paper layer 11 is positioned underneath and adjacent to the tray 30. The paper layer pulls moisture away from the wrap 40 and retains any residual moisture toward the tray 30. The moisture is free to spread out through the paper to increase the surface area of the moisture and thereby increase the rate of evaporation. The foam layer 12 advantageously cushions the tray and protects any sterilization wrap 40 or cart that may be used.

A method for sterilizing instruments 20 according to the present invention includes positioning the tray liner 16 in the base of the tray 30 such that the paper layer 11 is adjacent to the tray base 32 and positioning instruments on the foam layer 12. The types of instruments 20 that may benefit from sterilization method disclosed herein include all conventional surgical instruments composed of stainless steel. Determinations as to the types of surgical instruments to be placed on the tray 30, the numbers/weights of such surgical instruments, sterilization cycles, and the like, are made according to conventional sterilization criteria.

Tray 30 is then advantageously wrapped in a conventional sterilization wrap 40. Sterilization wrap 40 may be fabricated from paper and, optionally, a second absorbent tray liner 16 or other cushioning member may be placed between tray 30 and sterilization wrap as a base pad, thereby reducing the risk that wrap 40 may be torn by the corners of tray 30. Once wrapped in the sterilization wrap 40, tray 30 is ready to be placed in a sterilization unit for sterilization of surgical instruments 20. At the conclusion of the sterilization cycle, tray 30 is typically removed from the sterilization unit (not pictured), and the sterilized instruments 20 are, in due course, removed from the tray and made ready for subsequent surgical procedures. At the conclusion of the sterilization cycle, the absorbent tray liner 16 of the present invention is typically disposed of in a conventional waste container.

A preferred method for sterilizing instruments 20 according to the present invention includes positioning the liner 16 underneath the outer base of the tray 30 such that the paper layer 11 is adjacent to the tray base 32 and the foam layer 12 is not in contact with the tray 30. As such, the foam layer 12 may contact a sterilization wrap 40, if utilized. The paper layer 11 will absorb moisture that leaks through perforations in the base 32 of the tray 30. The paper layer 11 may also collect moisture that accumulates on the tray 30 surfaces. Moisture from the tray 30 or base 32 will be absorbed by the paper layer 11 and dissipate throughout its surface keeping the foam layer 12 appreciably dry, and in turn keeping sterilization wrap 40 dry and uncompromised.

With reference to FIG. 4, in a particularly preferred method where the liner 16 functions as a base pad, the perforations 13 are adapted to meet the tray 30 edges. This allows the edges of the liner 16 to be folded upward so that paper layer 11 is adjacent and in contact with the face 33 of the tray 30. This method allows for cushioning and moisture absorption from the face 33 of the tray as well as the base 32. Moisture from the tray 30 will be absorbed by the paper layer 11 and dissipate throughout its surface keeping the foam layer 12 appreciably dry, and in turn keeping sterilization wrap 40 dry and uncompromised.

Corner relief is provided through the perforations 13. The intersection of the longitudinal perforations 13a and the latitudinal perforations 13b may provide a corner box 17 within a sheet of liner 16. The corner box 17 may be easily removed through means of the perforations. Once the corner box 17 is removed, the sides of the liner 16 are more easily folded up and positioned adjacent to the tray face 33.

For additional corner relief, the liner of the invention may be provided with surface cuts 15. Various size cuts 15 are embodied. The surfaces cuts 15 are positioned to accommodate the edges of a sterilization tray 30, and most preferably the corners of the tray 30. The cuts 15 also allow for stabilization of a tray 30 while seated on the liner 16.

The absorbent tray liner of the present invention provides significant benefits to the reliability and efficacy of conventional sterilization operations. Ideally, as is known in the art, when the sterilization system is operating at peak performance a sterilization system that utilizes steam or ethylene oxide as the sterilizing agent will be totally dry at the conclusion of the sterilization cycle. However, as discussed above due to ambient humidity, plumbing, etc., sterilization systems are highly variable in operation and such systems do not always operate at peak levels. As a result, without use of an absorbent tray liner, it is not uncommon for residual moisture to be found on the surface of sterilized instruments or the sterilization tray at the conclusion of the sterilization cycle. The absorbent tray liner of the present invention exhibits sufficient hydrophilicity to absorb an amount of moisture sufficient to address typical operative variability.

The present invention, therefore, provides an absorbent liner 16 that functions to cushion trays and surgical instruments in connection with the sterilization process, and further functions to absorb potential excess moisture that might remain on the surgical instruments or on the tray at the conclusion of a steam or ethylene oxide sterilization process. The absorbent liner has been found to permit proper air removal, sterilant penetration/evacuation, and delivery of sterilized surgical instruments substantially devoid of residual moisture at the conclusion of a sterilization process. The absorbent tray liner has also been found to permit effective aeration of instruments sterilized with ethylene oxide.

Figure 6:
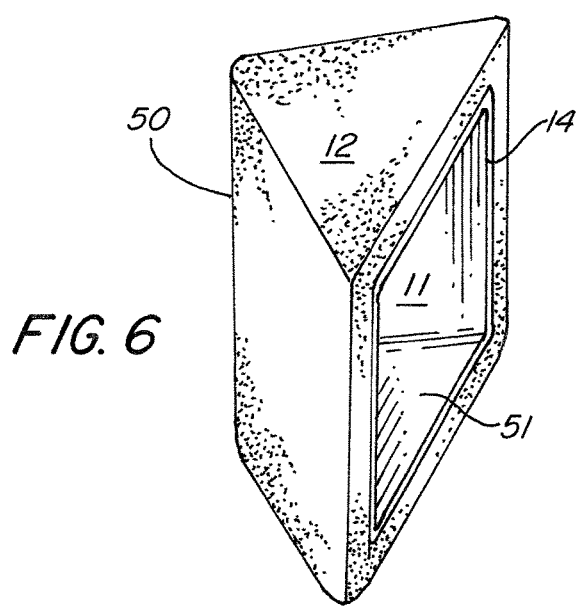
FIG. 6 is a perspective view of a corner guard according to the present invention.
Figure 7:
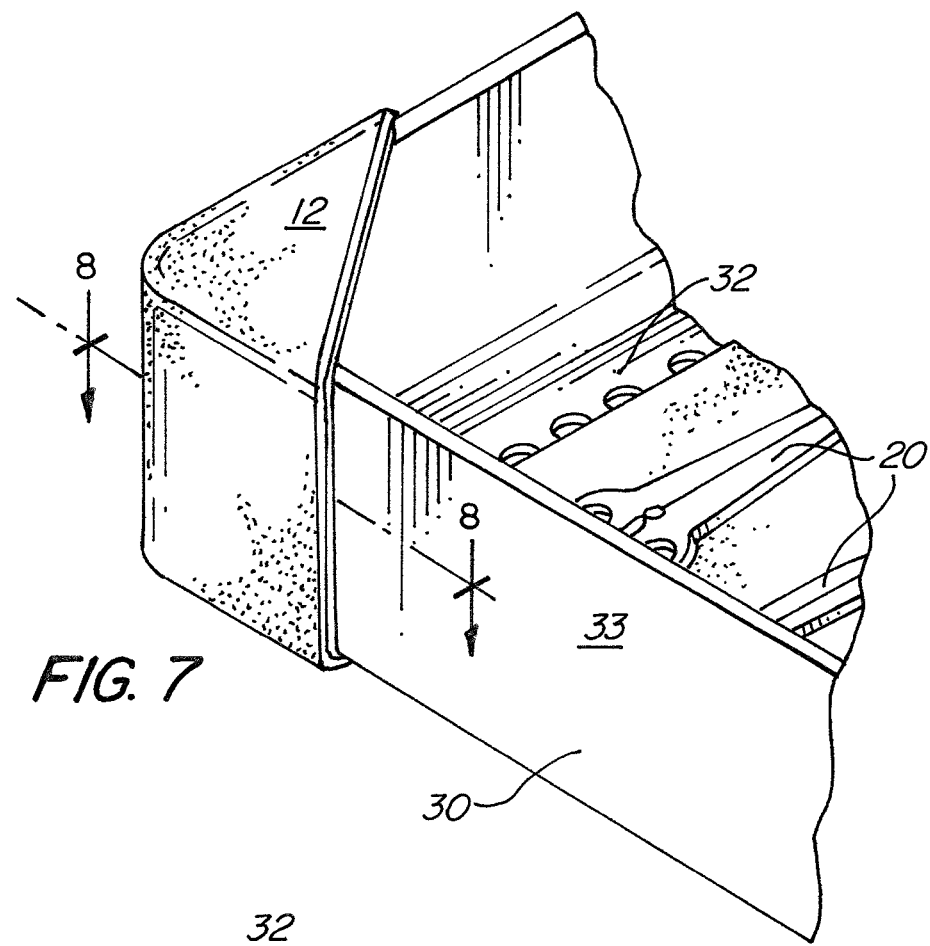
FIG. 7 is a perspective view of a corner guard according to the present invention positioned on the sterilization tray of FIG. 4.
Figure 8:
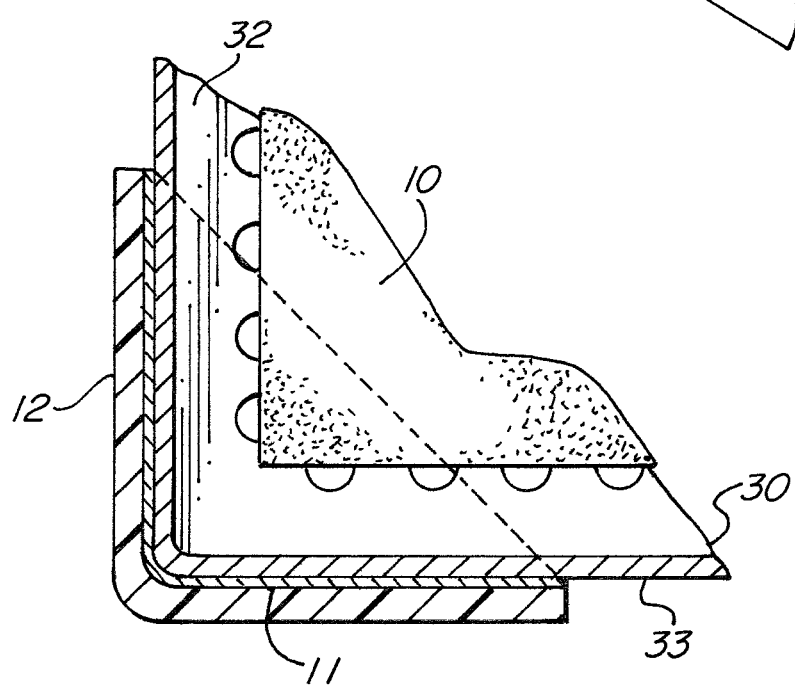
FIG. 8 is top-down view of a cross section of a corner guard according to the present invention positioned on the sterilization tray of FIG. 4.

Another embodiment of the liner in accordance with the present invention is illustrated in FIGS. 6-8. In particular, a corner guard 50 is provided which is preferably composed of a polyurethane foam layer 12 and a paper layer 11 as described above in connection with the liner 16. In addition, the corner guard is dimensioned for use with a sterilization tray such as that shown in FIGS. 2 and 4.

As shown in FIG. 6, guard 50 contains a cavity 51 that is shaped to accommodate the corner of tray 30. The paper layer 11 is exposed on the surface of the cavity 51. The outer surface of the guard 50 is comprised of foam layer 12.

Referring now to FIGS. 7 and 8, the guard 50 is positioned adjacent to the surface 33 of tray 30 is such that the paper layer 11 is adjacent to the surface 33. The corner guard 50 advantageously absorbs liquid while allowing the passage of the sterilization medium therethrough. The moisture is free to spread out through the paper to increase the surface area of the moisture and thereby increase the rate of evaporation. Thus, moisture is retained in the paper layer 11 before it reaches a sterile wrap or cart. Additionally, cushioning and protection are provided for the tray 30 and penetration of sterilization wrap by sharp corners is prevented.

The principles, preferred embodiments and modes of operation of the presently disclosed absorbent liners, corner guards and methods of sterilizing surgical instruments have been described in the foregoing specification. The presently disclosed absorbent liners and methods of sterilization, however, are not to be construed as limited to the particular embodiments shown as these embodiments are regarded as illustrious rather than restrictive. Moreover, variations and changes may be made by those skilled in the art without departing from the spirit of the presently disclosed absorbent liners, guards and methods of sterilization.

What is claimed is:

1. A two-ply liner for a surgical instrument sterilizing system, comprising:
    a foam layer fabricated from absorbent hydrophilic polymer; and
    a medical grade paper layer, suitable for use in terminal sterilization of surgical instruments, flame laminated to the foam layer, said medical grade paper being absorbent to moisture and permeable to sterilization steam and ethylene oxide.

2. The liner of claim 1, wherein the polymer is polyester polyurethane foam.

3. The liner of claim 1, wherein the liner further comprises perforations.

4. The liner of claim 3, wherein the liner has a length and a width, wherein the perforations include a plurality of lines of perforations each extending across the width, the lines being equally spaced at least 2 inches apart along the length of the liner.

5. The liner of claim 1, wherein the liner has a thickness, wherein the thickness of the liner is between 0.1 inches to 1 inch.

6. The liner of claim 5, wherein the thickness is about ⅛ of an inch.

7. The liner of claim 1, wherein the liner has a width, wherein the width of the liner is between 9 inches and 15 inches.

8. The liner of claim 1, provided in continuous roll form.

9. An apparatus for protection and moisture absorption in surgical instrument sterilizing systems, comprising:
    a tray having a bottom including an interior surface and an exterior surface, and sidewalls extending upward from the interior surface of the bottom;
    the liner of claim 1 within said tray for receiving surgical instruments thereon;
    wherein said paper layer is against the interior surface of the bottom of said tray and said foam layer is opposite said paper layer, facing upward, for receiving the surgical instruments thereon.

10. The apparatus according to claim 9, further comprising:
    a sterile wrap around said tray and the liner.

11. An apparatus for protection and moisture absorption in surgical instrument sterilizing systems, comprising:
    a corner guard formed in a shape with a triangular top, a triangular bottom, and sidewalls extending between two sides of the triangular top and bottom delimiting an interior cavity for receiving a corner of a sterilization tray;
    the corner guard having a foam layer fabricated from absorbent hydrophilic polymer and a medical grade paper layer, suitable for use in terminal sterilization of surgical instruments, flame laminated to the foam layer, said medical grade paper being absorbent to moisture and permeable to sterilization steam and ethylene oxide;
    wherein the foam layer defines exterior surfaces of the triangular top, the triangular bottom, and the two sidewalls, and the medical grade paper layer defines interior surfaces of the triangular top, the triangular bottom, and the two sidewalls in the interior cavity.

12. The apparatus according to claim 11, further comprising:
    a tray having tray corners, wherein the corner guard is positioned around one of the tray corners with said paper layer against the one of the tray corners; and
    a sterile wrap around said tray and the corner guard.

13. An apparatus for protection and moisture absorption in surgical instrument sterilizing systems, comprising:
    a sterilization tray having a bottom, including an interior surface and an exterior surface, and sidewalls extending upward from the interior surface of the bottom;
    the liner of claim 1 positioned below said sterilization tray such that the medical grade paper layer of the liner is against the exterior surface of the bottom of the sterilization tray.

14. The apparatus according to claim 13, further comprising:
    a sterile wrap around the tray and said liner.

15. The apparatus according to claim 13, further comprising:
    a second liner including a second foam layer fabricated from absorbent hydrophilic polymer and a second medical grade paper layer, suitable for use in terminal sterilization of surgical instruments, flame laminated to the second foam layer, said second medical grade paper being absorbent to moisture and permeable to sterilization steam and ethylene oxide;
    wherein said second liner is within the tray with the second medical grade paper layer against the interior surface of the bottom of the tray.

16. The liner according to claim 1, wherein the absorbent hydrophilic polymer has a tear resistance of at least 1.2 pounds per linear inch (pli).

17. The liner according to claim 1, wherein the absorbent hydrophilic polymer has a tensile strength of at least 17 pounds per square inch (psi) with at least 70% retention of the tensile strength after 3 hours at 105 C in a steam autoclave.

18. A continuous roll of two-ply liner material for a surgical instrument sterilizing system, consisting essentially of:
    a foam layer fabricated from absorbent hydrophilic polymer having a first side and a second side; and
    a medical grade paper layer, suitable for use in terminal sterilization of surgical instruments, flame laminated to the first side of the foam layer, said medical grade paper being absorbent to moisture and permeable to sterilization steam and ethylene oxide;
    a plurality of lines of perforation each extending across a width of the two-ply liner material, the lines being equally spaced apart along a length of the two-ply liner material.

19. The liner according to claim 18, wherein the absorbent hydrophilic polymer has a tensile strength of which at least 70% is retained after 3 hours at 105 C in a steam autoclave.

20. The liner of claim 18, wherein the liner material has a thickness between 0.1 inches to 1 inch and the width is between 9 inches and 15 inches.

* * * * *